(12) United States Patent
Kritzler et al.

(10) Patent No.: US 9,480,761 B2
(45) Date of Patent: Nov. 1, 2016

(54) PRION DISINFECTION

(75) Inventors: Steven Kritzler, Cronulla (AU); Alex Sava, Paddington (AU); Michael Zalunardo, Koonawarra (AU)

(73) Assignee: Novapharm Research (Australia) Pty Ltd., Rosebery, New South Wales (AU)

( * ) Notice: Subject to any disclaimer, the term of this patent is extended or adjusted under 35 U.S.C. 154(b) by 1874 days.

(21) Appl. No.: 10/467,591

(22) PCT Filed: Jan. 31, 2002

(86) PCT No.: PCT/AU02/00092
§ 371 (c)(1),
(2), (4) Date: Dec. 22, 2003

(87) PCT Pub. No.: WO02/062400
PCT Pub. Date: Aug. 15, 2002

(65) Prior Publication Data
US 2004/0106188 A1    Jun. 3, 2004

(30) Foreign Application Priority Data
Feb. 7, 2001 (AU) ..................... PR2938

(51) Int. Cl.
C12N 1/22 (2006.01)
C12N 1/20 (2006.01)
A61L 2/12 (2006.01)
A01N 63/00 (2006.01)
A61L 2/00 (2006.01)
A61L 2/025 (2006.01)
A61L 2/08 (2006.01)
A61L 2/16 (2006.01)

(52) U.S. Cl.
CPC ............... *A61L 2/12* (2013.01); *A01N 63/00* (2013.01); *A61L 2/0082* (2013.01); *A61L 2/025* (2013.01); *A61L 2/085* (2013.01); *A61L 2/16* (2013.01); *A61L 2202/24* (2013.01)

(58) Field of Classification Search
CPC ............ C11D 3/386; C12Y 304/21062
USPC ............ 435/262–279; 424/94.1–94.67
See application file for complete search history.

(56) References Cited

U.S. PATENT DOCUMENTS

| | | | | |
|---|---|---|---|---|
| 3,706,674 A | * | 12/1972 | Clark | 510/320 |
| 4,456,544 A | * | 6/1984 | Lupova et al. | 510/161 |
| 4,481,190 A | * | 11/1984 | Nestor et al. | 514/9.8 |
| 5,527,487 A | * | 6/1996 | Mikkelsen et al. | 510/393 |
| 2004/0091474 A1 | | 5/2004 | Raven et al. | |

FOREIGN PATENT DOCUMENTS

| | | | | |
|---|---|---|---|---|
| CN | 1170035 A | * | 1/1998 | ............ C11D 3/42 |
| CN | 1279954 A | | 1/2001 | |
| EP | 0 358 500 A1 | | 3/1990 | |
| EP | 0 742 018 A2 | | 11/1996 | |
| WO | WO 99/42829 | | 8/1999 | |
| WO | WO-99/51279 | | 10/1999 | |
| WO | 02/053723 A2 | | 7/2002 | |
| WO | WO-02/053723 A2 | | 7/2002 | |

OTHER PUBLICATIONS

Lemmer et al., 2004, Journal of General Virology, 85, 3808-3816.*
Lemmer et al., 2008, Journal of General Virology, 89, 348-358.*
Derwent, Abstract for CN 1170035A, 1998, Derwent Accession No. 2003-257446.*
EPO, Machine Translation of CN 1170035A, pp. 1-12.*
International Search Report, PCT/AU02/00092; May 3, 2002.
Bolton, Molecular Characteristics of the Major Scrapie Prion Protein, Blochemicstry, 1984, pp. 5898-5906, American Chemical Society, 1984.
Diener, Viroids and Prions, Proc. Natl. Acad. Sci. USA, vol. 79, pp. 5220-5224, Sep. 1982, Biochemistry.
Kocisko, Partial Unfolding and refolding of Scrapie-Associated Prion Protein: Evidence for a Critical 16-kDa C-Terminal Domain, Biochemistry 1996, pp. 13434-13442.
Riesner, Disruption of Prion Rods Generates 10-nm Spherical Particles Having High α-Helical Content and Lacking Scrapie Infectivity, Journal of Virology, Mar. 1996, pp. 1714-1722.
Extended European Search Report for Corresponding European Patent Application No. 10152838.8, mailed on May 20, 2010.
English-Language Abstract of Chinese Patent Application No. 200119170 (CN Publication No. 1279954 A).
Deslys, J. P. "[Risk prevention of transmissible subacute spongiform encephalopathies]." La Revue du praticien 49, No. 9 (1999): 966-970.
Taylor, D. M. "Inactivation of prions by physical and chemical means." Journal of Hospital Infection 43 (1999): S69-S76.
Taylor, D. M. "Inactivation of transmissible degenerative encephalopathy agents: a review." The Veterinary Journal 159, No. 1 (2000): 10-17.
Supplementary European Search Report, Feb. 16, 2004.
Prusiner et al., "Purification and structural studies of a major scrapie prion protein," Cell, Aug. 1984, 127-134, vol. 38.
Bajorath et al., "Autolysis and inhibition of proteinase K, a subtilisin-related serine proteinase isolated from the fungus Tritirachium album Limber," Abstract from Biochem. Biophys. Acta, May 18, 1988, 176-182, vol. 954, No. 2.

* cited by examiner

*Primary Examiner* — Sharmila G. Landau
*Assistant Examiner* — Sheridan Macauley
(74) *Attorney, Agent, or Firm* — Locke Lord LLP

(57) ABSTRACT

The invention relates to a methods and compositions for treating a surface, suspension or solution contaminated with a $PrP^{Sc}$ prion protein or a surrogate thereof. The methods and compositions employ a combination of one or more enzymes effective to cleave a prion protein to fragments having a non-infective molecular weight, and one or more agents selected to favor conformational unfolding of the $PrP^{Sc}$ prion protein while not denaturing the one or more enzymes.

15 Claims, No Drawings

PRION DISINFECTION

CROSS REFERENCE TO RELATED APPLICATIONS

This application is a 371 of PCT/AU02/00092, filed Jan. 31, 2002, which claims priority to Australian Patent Application No. PR2938, filed Feb. 7, 2001, both of which are incorporated by reference herein in their entirety.

FEDERALLY SPONSORED RESEARCH STATEMENT

Not applicable.

REFERENCE TO MICROFICHE APPENDIX

Not applicable.

TECHNICAL FIELD

This invention relates to compositions and methods for inactivating prions and to means for disinfecting materials contaminated by prions or by similar conformationally altered proteins.

BACKGROUND OF THE INVENTION

Historically, infectious agents such as bacteria, fungi, parasites, and viroids have well established methods of control that involve various forms of disinfection and sterilization (e.g. steam sterilization, dry sterilization, pasteurization, sterile filtration, treatment with ethylene oxide, glutaraldehyde, phenols or other disinfecting chemicals, radiation, etc.). With viruses, there are also established methods for example lowering the pH to 4.0 or below, heating at 60° C. for extended periods, or use of organic solvents in high concentrations. In addition, UV treatment, formaldehyde and specific antiviral agents have been employed.

For some years now, new and previously unknown species of pathogenic agents have appeared and have been reported in scientific publications. These have been referred to as prions and present one of the greatest challenges facing the health care industry today. Prions are infectious particles that differ from bacteria and other previously known infectious agents. While there is no firm evidence on the exact structure of prions, a number of diseases have been identified recently both in humans and animals, that appear to be attributable to prions. As detailed in PCT/US00/14353 (the content of which is incorporated herein by reference), human diseases attributed to prions include Kuru, Creutzfeldt-Jakob disease (CJD), Gerstmann-Straussler-Scheinker disease (GSS), and Fatal Familial Insomnia. (FFI).

In addition to prion diseases of humans, disorders of animals are included in the group of known prion diseases. Scrapie of sheep and goats is perhaps the most studied animal prion disease. Several lines of inquiry have suggested a link between variant CJD and a preceding epidemic of bovine spongiform encephalopathy (BSE). No successful therapeutic treatments have been developed and as a result these diseases are always fatal. Adding to the problem is the fact that the incubation period can be up to 30 years in humans and this factor presents a major challenge to the scientists involved, with some predicting an epidemic "in the pipeline".

Groups possibly at risk of infection include patients who may come into contact with infected medical instruments during surgery, medical staff dissecting infected material, and healthcare workers responsible for cleaning and sterilizing instruments. There are also concerns that groups at risk may be broadened to include veterinarians, abattoir workers, butchers in contact with cows or beef primarily in Europe and more recently persons receiving blood transfusions or organs from donors incubating a prion disease.

The structure of prions has been the subject of intense investigation and different points of view have been expressed. Some scientists believe they are extremely small viruses, while most experts now believe that prions are actually infectious proteins without a DNA or RNA core. More particularly the consensus now is that the PrP gene of mammals expresses a protein which can be the soluble, non-disease, cellular form $PrP^c$ or can be an insoluble disease form $PrP^{Sc}$. Many lines of evidence indicate that prion diseases result from the transformation of the normal cellular form into the abnormal $PrP^{Sc}$ form. There is no detectable difference in the amino acid sequence of the two forms. The $PrP^c$ form is composed of a highly membrane associated 33-35 kDa protein which degrades on digestion with protease K. However the $PrP^{Sc}$ form has an altered conformational form, in particular having a high level of β-sheet conformation. Properties of $PrP^{Sc}$ useful in diagnosing the infective altered conformational form are a protease resistant core of 27-30 kDa. Another distinctive feature of the altered conformational infective form is that it acquires a hydrophobic core.

Conventional disinfection and sterilizing agents have no significant effect on prions in an acceptable time. Attempts to deactivate prions and/or to disinfect surfaces on which they may be transmitted have shown an extraordinary resistance. The conditions required are generally too severe to be practical for routine disinfection, not only in terms of time and cost, but also in terms of damage to materials and occupational health hazards involved. For example in one study infectious $PrP^{Sc}$ particles have been detected in a sample after 5-15 mins/600° C. dry heat although total destruction could be achieved at 1000° C. in 15 mins and in from 1-10 hrs at >200° C. It has been proposed to treat with I M. caustic soda (pH14) for 2 hrs but that treatment is extremely corrosive, dangerous to staff, and aggressive to materials. U.S. Pat. No. 5,633,349 describes a procedure for treating a biological material involving treatment with 6-8 molar urea or 1-2 molar sodium thiocyanate for a minimum of 12 hrs (preferably 18 hrs) which suffers from similar disadvantages.

Because of the difficulties in decontamination it has been proposed as preferably that surgical instruments used in brain surgery should be used only once, but this implies a disposal risk in addition to being expensive and for some instruments impractical. PCT/US00/14353 describes a method of rendering prions non-infectious by use of a polycationic dendrimer but it is not clear whether that process is reversible or permanent or commercially viable for disinfecting surfaces.

Although attention has been focused on the $PrP^c$ form and the $PrP^{Sc}$ form it has also been suggested that the protein can exist in an intermediate form which has a β-sheet content intermediate between the predominantly alpha helix structure of the $PrP^c$ form and the predominantly β-sheet conformation of the $PrP^{Sc}$ form and which retains solubility in the absence of a denaturant.

The assembly or misassembly of normally soluble proteins into conformationally altered insoluble proteins is thought to be causative of, or implicated in, a variety of other diseases. Although the invention will be herein described in relation to prions, it will be understood to be applicable to other insoluble or enzyme resistant conformationally altered proteins implicated in disease.

The above discussion of prior art is not to be construed as an admission with regard to the common general knowledge in Australia.

SUMMARY OF THE INVENTION

An object of the invention is to provide improved, or at least alternative, means of disinfecting a surface infected with prions. In certain preferred embodiments, the invention renders prions inactive more efficiently, that is to say more effectively in a given time, or as effectively in a shorter time, than prior art methods. Certain highly preferred embodiments of the invention achieve better than a 4 log reduction in less than 60 mins at below 60° C. In some embodiments the invention is also applicable to prions in situations other than on surfaces for example in suspension in a solid, liquid or gaseous medium or in biological systems and may have other in vitro or in vivo uses. It is an object of some embodiments of the invention to provide improved diagnostic tools and of other embodiments to provide novel epimers for preparation of antibodies.

The term "prion protein" as herein used includes variants, fragments, fusions, and analogues that have other interactions or activities that are substantially the same as those of a full length prion protein sequence, but which may be more convenient to use and includes all forms of secondary structure The term is also herein used to include prion surrogates, that is to say proteins which are not themselves prions but which have similar structure or exhibit similar behaviour to prions and can be used to model or predict how a prion would perform under specified conditions. The term "PrP$^{Sc}$ prion protein" is intended to have a similarly broad meaning but is limited to prion proteins which by virtue of their secondary or tertiary structure are enzyme resistant and includes conformations which are similarly enzyme resistant

BRIEF DESCRIPTION OF THE DRAWINGS

Not applicable.

DESCRIPTION OF EMBODIMENTS OF THE INVENTION

According to a first aspect the invention provides a method of disinfection comprising the steps of treating a surface contaminated with a PrP$^{Sc}$ prion protein or a surrogate thereof simultaneously with a combination of (1) one or more enzymes effective to cleave a prion protein to fragments having a non-infective molecular weight, and (2) one or more agents selected to favour conformational unfolding of the PrP$^{Sc}$ prion protein while not denaturing the one or more enzymes.

According to a second aspect the invention provides a method according to the first aspect, further including (3) one or more agents selected to promote or protect folding of the one or more enzymes, without preventing cleavage of the prion protein. Preferably, the conditions are selected to favour unfolding over refolding.

It is presently accepted that proteins having a molecular weight of less than 27 kDa are non-infective and safe, and accordingly the method of the invention envisages digestion or cleavage of the prion to fragments of which at least 90% and preferably at least 98% are less than 27 kDa, and preferably less than 25 kDa or more preferably less than 23 kDa. However, if in the future a protein of less than 27 kDa should be found to be infective, the method of the invention could be utilized to fragment the protein to fragments of any safe size.

The term "prion surrogate" as used herein is according to the FDA definition, that is to say, proteins having a similar resistance to proteases due to the presence of β-folding. The term "agent" is herein used to include both chemical reagents for example anionic surfactants, reagents to modify pH, and also non-chemical agents which effect physical and/or thermodynamic conditions such as pressure, temperature, irradiation and other energetic influences which promote folding, or unfolding, as the context requires. Folding agents are sometimes referred to as "refolding" agents. Unfolding agents are sometimes referred to as "denaturing" agents According to a third aspect the invention provides a method according to the first or second aspect wherein said one or more agents selected to favour conformational unfolding includes one or more agents selected from the group consisting of irradiation, electric field, magnetic field, energetic vibration and combinations thereof.

In highly preferred embodiments of the invention a combination of chemical and physical agents is employed, for example the agents of step (2) include an anionic surfactant in combination with sonication by ultrasound.

For preference the prion is subjected to sound waves in the ultrasonic range during the treatment. However the unfolding may be induced or aided by other forms of radiation such as microwave radiation, radiation in the radiofrequency, infra red, visible or U.V spectrum, sound at audible or lower frequency, energetic vibration from mechanical means such as magnetic or vortex stirring. Other forms of energetic input may include from electron beam irradiation, laser irradiation, or electrolysis.

According to other aspects, the invention extends to include compositions for use in conducting the method, to novel prion fragments produced by the method and to novel antibodies produced from said fragments According to the invention a contaminated surface, for example a surgical instrument contaminated with a PrP$^{Sc}$ protein, is treated with a combination of (1) one or more enzymes effective to cleave the prion protein into fragments of a non infective molecular weight, (currently, less than 27 kDa), and (2) one or more agents selected to favour conformational unfolding of the prion protein PrP$^{Sc}$ protein is characteristically resistant to attack by enzymes including proteolytic enzymes. Without wishing to be bound by theory, the present inventors supposed that the resistance of PrP$^{Sc}$ protein to attack by enzymes is a consequence of the folded conformation (having a high ratio of β-sheet secondary structure relative to alpha helix structure). The invention involves the conception that it is possible to select one or more agents so as to promote, under selected conditions, unfolding of the PrP$^{Sc}$ protein sufficiently for an enzyme to gain access and cleave PrP$^{Sc}$ protein.

Many proteins are prone to loose their natural three dimensional folding pattern ("secondary and tertiary structure") and to become "denatured". The denaturation includes breakdown of the intramolecular interaction, especially hydrogen and disulphide bonds, and thus the loss of the secondary structure which virtually all native proteins have in at least parts of the molecule, and which generally is decisively responsible for the activity of the protein.

Those skilled in the art appreciate that enzymes are themselves proteins and tend to be readily denatured by agents which promote protein unfolding. It is not clear whether that is because the unfolding agent binds to the enzyme, preventing the enzyme from binding to a target substrate, or more likely because the unfolding agent promotes unfolding of the enzymes conformational structure, rendering it inactive or "denatured" or a combination of those effects. $PrP^{Sc}$ protein on the other hand is highly resistant to unfolding. It has hitherto been considered impossible to formulate a system in which an enzyme retains activity in the presence of an unfolding agent effective to influence such an intractable protein as $PrP^{Sc}$. Surprisingly the present inventors have found that either (i) certain unfolding agents selectively unfold or relax the $PrP^{Sc}$ protein while not unfolding (denaturing) a selected enzyme or (ii) that folding and unfolding agents can be combined in such a way that the folding agent selectively promotes or retains enzyme activity, while the unfolding agent selectively and sufficiently unfolds the prion to provide access to the enzyme for prion scission.

These intrinsically conflicting desiderata are met in the present invention by classifying agents as promoting "folding" or "unfolding" and then determining their relative effect on enzymes and on $PrP^{Sc}$ protein or a surrogate thereof.

The surface may be first treated with the one or more agents and the one or more enzymes may be added subsequently but in preferred embodiments the surface undergoing treatment is subjected to both simultaneously.

The enzyme is preferably a proteolytic enzyme. Suitable enzymes are:

- non-specific proteinases:—e.g. serine-, aspartic-, metalloproteinases
- more specific proteinases—e.g. keratinases, collagenases etc
- any other enzyme(s) that posses proteolytic activity The one or more agents selected to favour conformational unfolding of the prion protein are chosen to be effective to provider access by the enzyme to the prion protein. In general the folding-unfolding of a polypeptide chain may be a thermodynamically reversible equilibrium process or may be irreversible.

By way of example only, agents which promote unfolding (denaturation) include:

(1) heat—increases in temperature up to about 150° C.

(2) pH—values below 3 and above 9 (global effect resulting from ionization of many side chain residues accessible to the solvent) or in some molecules may be attributable to local effects due to ionization of specific groups (e.g. serine proteases due ionization of N-terminal amino group of the carboxylate)

(3) Selected organic solvents of a kind which tend to denature, dissolve or swell proteins. Generally the products are not completely unfolded and possess an ordered conformation which differs from the native state. Solvents which favour helical conformations (i.e. unfolding) are exemplified by N-dimethylformamide, formamide, m-cresol, dioxan, $CHCl_3$, pyridine, dichlorethylene, and 2-chloroethanol. This group also includes solvents which have a weak tendency to form hydrogen bonds such as the alcohols, ethanol, n-propanol, methanol (especially in mixture with 0.01% HCl), Also, solvents which tend to disorganize the structure e.g. dimethylsulphoxide (DMSO) at high concentrations, dichloroacetic acid and trifluoroacetic acid, and other electrophillic solvents (4) Certain organic solutes and chaotropic agents.—Such as urea, guanidine hydrochloride (GuHCl). The transition to randomly coiled polypeptide is complete for 6-8M GuHCl at room temp except for some exceptionally stable proteins. These agents may be markedly influenced by temperature, pH other reagents and conditions.

(5) Certain surfactants—Ionic surfactants tend to bind to proteins and initiate unfolding of tertiary structure. Anionic detergents are very strong denaturants. E.g. Sodium dodecyl sulfate (SDS) is able to completely unfold many (but not all) proteins at concentrations close to the critical micelle concentration. Dodecyl benzene sulfonate is also a denaturant. The detergents do not necessarily result in a complete unfolding since in some cases it appears that the hydrophobic part of the detergent might interact with the ordered structure of the protein to form micellar regions. Cationic surfactants are usually less effective unfolding agents than anionic. Dodecyl ethoxy sulfates tendency to denature bovine serum albumin (BSA) decreases with increasing ethoxy groups and disappears for ethoxy greater than six (6) Inorganic salts can induce conformational transitions in proteins. For example LiBr, $CaCl_2$, KSCN, NaI, NaBr, sodium azide are strong denaturants. Although these salts do not necessarily lead to completely unfolded protein, the residual ordered structure may be disrupted by energy input e.g. increasing temperature. Anions such as $CNS^- > I^- > Br^- > NO_3^- > Cl^- > CH_3COO^- > SO_4^-$ exhibit similar behaviour as do guanidinium salts and tetraalkyl ammonium salts However $(GuH)_2SO_4$ has been observed to protect certain proteins against denaturation.

(7) agents which cause scission of the S—S bond such as thioglycols (8) Other substances with strong affinity to either hydrophilic or hydrophobic residues of amino acids (9) Adsorption on certain surfaces and interfaces including zeolites, including air/liquid interfaces. These include, for example, but are not limited to: finely divided alumina, silicas and other chromatographic and stationary phases.

(10) Ultrasonic energy, Infra red and microwave radiation, high pressure, and subjecting protons to the action of electric and/or magnetic fields may be able to promote unfolding (refolding), and even shaking or stirring may be influential.

In preferred forms of the invention a combination of agents is used for example a surfactant and/or a suitable solvent with ultrasound is employed. It is unclear whether the input of energy, such as from ultrasound, assists in driving the folding/unfolding equilibrium in favour of unfolding of the $PrP^{Sc}$ protein at a greater rate than it does in denaturing the enzyme, or whether it merely assists in providing access of the reagents or enzymes to the prion, or whether it is effective in activating the enzyme. Other methods of applying energy include application of sound waves in the sub-sonic range. However energetic vibration may be induced by other forms of electromechanical radiation or energetic vibration from mechanical means such as magnetic or vortex stirring. Other forms of energetic input may include from electron beam irradiation, laser, or electrolysis.

As indicated above, most of the discussed unfolding agents would be expected effectively to denature the enzyme. Either the unfolding agent and its conditions of use must be carefully selected so as to permit digestion of the PrP$^{Sc}$ protein or its surrogate without denaturing the enzyme, or alternatively the unfolding agent must be combined with a folding agent.

Suitable folding agents include:
(1) Nucleophillic solvents and highly hydrogen bonded organic solvents. There is competition between the energy of the peptide hydrogen bonds and the strength of hydrogen bonds between solvent molecules. When solvent molecules are linked by strong hydrogen bonds the equilibrium is shifted to towards stabilization of peptide hydrogen bonds. Solvents such as dioxan, acetonitrile, dimethylformamide, pyridine, and, at low concentrations, dimethylsulphoxide (DMSO) which are good proton acceptors but weak proton donors have a very weak tendency to disrupt peptide hydrogen bonds and tend to induce ordered conformation, especially in globular proteins.

(2) Stabilizing solvents such as polyhydric alcohols (e.g. glycerol, ethylene glycol, and propylene glycol, sucrose and the like) which are weakly protic and in the presence of which proteins tend to remain conformationally stable and may be used as stabilizing agents.

(3) Non-ionic surfactants such as alkyl, phenyl or alkyl ethoxylates, propoxylates or copolymers thereof, alkylpolyglucosides etc, sarcosinates (e.g. sodium-(N-lauroyl) sarcosinate) do not alter the tertiary structure of protein and any unfolding occurs in the region of the isotherm where a significant increase in surfactant binding by non-specific cooperative interaction begins The effects of SDS can be reduced by addition of non-ionic or amphoteric surfactants (4) Zwitterionic and amphoteric surfactants, (5) High concentrations of buffers, (e.g. phosphates, acetates, citrates, borates)

(6) Surface active homo-, co-, or block-polymers which contain weakly hydrophobic and weakly hydrophilic zones in alternating arrangement, (7) Protective agents such as sulphated compounds, deoxycholate, glycosaminoglycans If a folding agent is combined with an unfolding (denaturing) agent then the agents and conditions must be selected to protect or refold the enzyme while irreversibly unfolding or at least opening the prion sufficiently for access by the enzyme. For example, the pH and/or temperature may be selected so that the folding agent acts selectively on the enzyme while the unfolding agent acts selectively on the $PrP^{Sc}$ protein.

Bovine albumin with high globulin content (Sigma product A7906), beta-galactosidase (G7279) and rabbit muscle myosin (M0163)) were used as models of proteins with low-solubility and high beta-sheet content. The molecular weight of the above proteins are significantly larger than that of the prions. The identifying of molecular mass of peptide fragments after enzymatic digest is easier, as most of proteases used in the experiment have molecular mass (20-35 KDa) similar to prions.

SDS-PAGE was conducted using the method described by Laemmli U.K., Nature, 227, pages 680-685, (1970). The protein solution was boiled for 2 min in sample buffer containing 2% SDS. 1.5 mm polyacrylamide slab gels (8-12%) were loaded with 10 microliters of the protein per lane, and subjected to non-reducing conditions (ie. no beta-mercaptoethanol in sample buffer). Electrophoresis was performed for 1 hour at 150 V, until the dye front was at the bottom of the gel. The gel was then removed and the protein bands visualized by staining either with Coomassie brilliant blue R-250 (Sigma) or silver stained (Bio-Rad). The molecular mass value for proteins was determined by using calibrating curve obtained with prestained low molecular weight markers (Bio-Rad marker 161-0318).

Cleaving the proteins was considered sufficient when no fragments with molecular mass larger than 14.4 KDa (the molecular weight of lysozyme) were detected after the combined action of unfolding agents and enzymes. That indicates that the treatment was effective on the surrogate.

When peptide fragments with molecular mass of larger than 14.4 KDa were present, the results was reported as positive To prove that the method of the invention may be used to deactivate prions, and not merely cleave the surrogate, the prion detection test developed by Prionics AG was employed.

The "Prionics-Check" is an immunological test for the detection of prions in animal tissues that use a novel antibody developed by PRIONICS AG. The $PrP^{Sc}$ remaining in the reaction mixture is bound by the antibody and detected using an enzyme coupled to the antibody.

100 mL aliquots of the solutions as described in table 1 were spiked with approx. 1 microgram of recombinant prion protein and the Prionics Check was performed as per the procedure described in Appendix 1.

When $PrP^{Sc}$ was detected after the enzymatic digest, the results were reported as positive. Table 1 shows that in control experiments 1-1 to 6-1 fragments having a mass greater than 14.4 KDa were detected as was $PrP^{Sc}$. However in experiments 1-2 to 6-2 no fragments were detected with a mass greater than 14.4 KDa and no $PrP^{Sc}$ was detected. 1-1 differs from 1-2 by inclusion of an unfolding agent (3% DOBS) shown to be effective in 30 min at 70° C.

2-2 and 3-2 differ from 2-1 and 3-1 respectively by inclusion of sonication. In 2-2 an unfolding agent 3% DOBS in combination with 25% Terric 164 (a folding agent) was effective at 25° C. with sonication at 40 kHz In 3-2 a similar result was obtained with 10% SDS as unfolding agent and a zwitterionic surfactant as folding agent at 2.6 mHz.

4-2 differs from 4-1 by the combination of borax with SDS at a more elevated temperature.

5-2 differs from 5-1 by combining DOBS with Triton X-100 in the absence of boron 6-2 differs from 6-1 by increasing the concentration of DMSO from reversibly unfolding (0.05%) to irreversibly unfolding (0.5%)

As will be apparent to those skilled in the art from the teaching hereof the invention may be performed using other combinations of agents without departing from the inventive concept herein taught.

TABLE 1

| No. | Test procedure/solutions | SDS-PAGE Albumin | SDS-PAGE beta-galacto sidase | SDS-PAGE myosin | Prionics Check |
|---|---|---|---|---|---|
| 1-1. | Distilled water<br>Warm to 70 C.<br>Keep in water bath at 70 C. for 30 min, 15 units protease activity per mL, pH 9<br>Cool down to 25 C. | + | + | + | + |
| 1-2. | 3% DOBS and Distilled water diluted 1:100<br>Warm to 70 C.<br>Keep in water bath at 70 C. for 30 min, 15 units protease activity per mL, pH 9<br>Cool down to 25 C. | − | − | − | − |
| 2-1. | 3% DOBS, 25% Teric 164, diluted 1:100<br>15 units protease activity per mL pH 9<br>25 C. for 30 min | + | + | + | + |
| 2-2 | 3% DOBS, 25% Teric 164 diluted 1:100<br>15 units protease activity per mL<br>sonicated with 40 kHz ultrasound<br>25 C. for 30 min | − | − | − | − |
| 3-1 | 10% SDS 10% Empigen BS/AU(zwitterionic surfactant) diluted 1:100<br>15 units protease activity per mL pH 9<br>25 C. for 30 min | + | + | + | + |
| 3-2 | 10% SDS 10% Empigen BS/AU(zwitterionic surfactant) diluted 1:100<br>15 units protease activity per mL pH 9<br>25 C. sonicated 2.6 mHz for 30 min | − | − | − | − |
| 4-1 | 10% SDS, 4% borax diluted 1:100<br>15 units protease activity per mL pH 9<br>25 C. for 30 min | + | + | + | + |
| 4-2 | 10% SDS, 4% borax diluted 1:100<br>15 units protease activity per mL pH 9<br>55 C. for 30 min | − | − | − | − |
| 5-1 | 15% DOBS, 5% Triton X100 4% Borax diluted 1:100<br>15 units protease activity per mL pH 9<br>25 C. for 30 min | + | + | + | + |
| 5-2 | 15% DOBS, 5% Triton X100 diluted 1:100<br>15 units protease activity per mL pH 9<br>25 C. for 30 min | − | − | − | − |
| 6-1 | .05% DMSO<br>15 units protease activity per mL pH 9<br>25 C. for 30 min | + | + | + | + |
| 6-2 | .5% DMSO<br>15 units protease activity per mL pH 9<br>25 C. for 30 min | − | − | − | − |

DOBS = dodecyl benzene sulfonic acid (Sigma Product No. D2525)
DMSO = dimethylsulfoxide (Sigma Product No. D5879)
Protease = Subtilisin Carlsberg (Sigma Product No. P5380)
Sonication at 40 kHz performed using ultrasonic bath supplied by UNISONICS Pty Ltd.
Sonication at 2.6 mHz performed using Disonics Pty Ltd. ultrasonic nebulizer.

APPENDIX 1

Prionics Check Test Method

The protocol below outlines using the protease resistant core of $PrP^{sc}$, from a recombinant source known to be representative of the naturally occurring infectious agent. It has been proven experimentally that the protease resistant core of the prion is not infectious, but indicates the presence of infectious agents 1. Weigh 1 microgram of $PrP^{sc}$ or BSE infected animal brain homogenate that contains 1 mcg or $PrP^{sc}$ and reconstitute it in 1 ml of deionised water
2. Add to 10 ml of test solution and subject to appropriate deactivation protocol
3. Take 10 microliter aliquot of the test solution and add it to 10 microliters of sample buffer
4. Perform SDS-PAGE of
   untreated $PrP^{sc}$ solution used for spiking (positive control)
   solution under study All proteins or protein fragments are separated in an electric field according to their size. The small proteins migrate faster than the large proteins. After a period of time the smallest fragments of the decomposed prion proteins migrate out of the gel while the resistant $PrP^{Sc}$ fragments will be present in the lower half of the gel. In the control sample where the prion protein remains resistant to protease, non-cleaved $PrP^{Sc}$ molecules will remain higher up in the gel.

1. Transfer proteins from the gel to nitrocellulose membrane by Western blotting.
2. Add monoclonal antibodies (Prionics Product No. 01-020).
3. Allow to bind to the proteins and then wash away non-bound antibodies.
4. The horseradish-peroxidase conjugated to primary antibodies is allowed to react with a chemoluminescence substrate (ECL product No. RPN 2209 supplied by AMERSHAM Life Science)
5. Expose the membrane to X-Ray film, develop the film.
6. Assess whether prion protein are present. Report results as positive when the antibodies are retained at the position corresponding to molecular mass of prion protein.

What is claimed is:

1. A non-therapeutic method of disinfection comprising the steps of treating a surface, suspension, or solution contaminated with a $PrP^{Sc}$ prion protein or a surrogate thereof simultaneously with a combination consisting essentially of:

(1) the serine protease subtilisin Carlsberg (SC); and (2) one of:

a) dodecyl benzene sulfonic acid (DOBS), a mixture of $C_{12}$ and $C_{15}$ alcohols poly (alkoxylated) with 6 mole ethylene oxide per mole and sonication;

b) sodium dodecyl sulfate (SDS), borax and a temperature from ambient temperature to about 150° C.; or c) DOBS and Triton-X 100;

wherein DOBS, SDS, temperature and sonication favor conformational unfolding of the $PrP^{Sc}$ prion protein while not denaturing the subtilisin Carlsberg, and the mixture of $C_{12}$ and $C_{15}$ alcohols poly (alkoxylated) with 6 mole ethylene oxide per mole, borax, and Triton X-100 promote or protect folding of the subtilisin Carlsberg, without preventing the cleavage of the prion protein; and wherein the pH of the composition is about pH 9.

2. A method according to claim 1, wherein the treatment is selected so as to result after cleavage in a predetermined percentage of the protein fragments having a molecular weight of less than a predetermined molecular weight.

3. A method according to claim 1, wherein at least 90% of the protein fragments after cleavage have a molecular weight of less than 27 kDa.

4. A method according to claim 1, wherein at least 90% of the protein fragments after cleavage have a molecular weight of less than 25 kDa.

5. A method according to claim 1, wherein at least 90% of the protein fragments after cleavage have a molecular weight of less than 23 kDa.

6. A method according to one of claims 1 to 5, wherein the conditions are selected to protect or refold the subtilisin Carlsberg while irreversibly unfolding or at least opening the prion sufficiently for access by the subtilisin Carlsberg.

7. A method according to claim 1, further including in the combination one or more agents selected to favor conformational unfolding of the $PrP^{Sc}$ prion selected from the group consisting of irradiation, electric field, magnetic field, energetic vibration and combinations thereof.

8. A method according to claim 7, wherein the energetic vibration is one or more of ultrasound, electromagnetic or mechanical vibration.

9. A method according to claim 1, further including in the combination one or more additional agents selected to promote unfolding of the $PrP^{Sc}$ prion protein, wherein the additional agent is selected from the group consisting of heat, pH, organic solvents which tend to denature proteins, chaotropic agents, surfactants tending to bind proteins, inorganic salts which are strong denaturants of proteins, agents which cause S—S bond scission, substances having a strong affinity for hydrophilic residues of amino acids, substances having a strong affinity for hydrophobic residues of amino acids, substances promoting adsorption on surfaces, and combinations of the foregoing.

10. A method according to claim 1, further including in the combination one or more folding agents selected from the group consisting of nucleophilic solvents, weakly protic stabilizing solvents, non-ionic surfactants, ionic surfactants, zwitterionic and amphoteric surfactants, buffers, surface active homo-, co-, or block-copolymers, sulphated compounds, deoxycholate, glycosaminoglycans and combinations of the foregoing.

11. A composition for treating a surface contaminated with a $PrP^{Sc}$ prion protein or a surrogate thereof, the composition consisting essentially of:

(1) subtilisin Carlsberg (SC); and (2) one of:

a) dodecyl benzene sulfonic acid (DOBS) and a mixture of $C_{12}$ and $C_{15}$ alcohols poly (alkoxylated) with 6 mole ethylene oxide per mole;

b) sodium dodecyl sulfate (SDS) and borax; or c) DOBS and Triton-X 100;

wherein DOBS and SDS favor conformational unfolding of the $PrP^{Sc}$ prion protein while not denaturing the subtilisin Carlsberg, and the mixture of $C_{12}$ and $C_{15}$ alcohols poly (alkoxylated) with 6 mole ethylene oxide per mole, borax, and Triton X-100 promote or protect folding of the subtilisin Carlsberg, without preventing the cleavage of the prion protein; and wherein the pH of the composition is about pH 9.

12. A composition according to claim 11, wherein one of a), b), c), or d) is selected so as to result after cleavage in a predetermined percentage of the protein fragments having a molecular weight of less than a predetermined molecular weight.

13. A composition according to claim 11, wherein one of a), b), c), or d) is selected so as to result after cleavage in at least 90% of the protein fragments after cleavage having a molecular weight of less than 27 kDa.

14. A composition according to claim 11, wherein one of a), b), c), or d) is selected so as to result after cleavage in at least 90% of the protein fragments having a molecular weight of less than 25 kDa.

15. A composition according to claim 11, wherein one of a), b), c), or d) is selected so as to result after cleavage in at least 90% of the protein fragments having a molecular weight of less than 23 kDa.

* * * * *